United States Patent [19]

Macdonald

[11] Patent Number: 5,721,247

[45] Date of Patent: Feb. 24, 1998

[54] ISOTHIOUREA DERIVATIVES USEFUL IN THERAPY

[75] Inventor: James Edwin Macdonald, Pittsford, N.Y.

[73] Assignee: Astra Aktiebolag, Sodertalje, Sweden

[21] Appl. No.: 535,102

[22] PCT Filed: Sep. 20, 1995

[86] PCT No.: PCT/SE95/01069

§ 371 Date: Nov. 14, 1995

§ 102(e) Date: Nov. 14, 1995

[87] PCT Pub. No.: WO96/09286

PCT Pub. Date: Mar. 28, 1996

[30] Foreign Application Priority Data

Sep. 20, 1994 [GB] United Kingdom ............... 9418912

[51] Int. Cl.$^6$ .............. C07C 335/32; C07D 217/06; A61K 31/155; A61K 31/47

[52] U.S. Cl. .............. 514/307; 514/309; 514/327; 514/331; 514/637; 546/141; 546/149; 546/231; 546/145; 564/245

[58] Field of Search ................ 546/145, 141, 546/149, 231; 514/307, 309, 327, 331, 637; 564/254

[56] References Cited

U.S. PATENT DOCUMENTS

| | | | |
|---|---|---|---|
| 2,050,552 | 8/1936 | Bockmuhl et al. | 424/322 |
| 4,008,330 | 2/1977 | Yamamoto | 514/342 |
| 4,211,867 | 7/1980 | Rasmussen | 424/322 |
| 4,785,008 | 11/1988 | Coquelet et al. | 424/322 |
| 5,223,498 | 6/1993 | Balasubramanian | 424/322 |

FOREIGN PATENT DOCUMENTS

| | | |
|---|---|---|
| 0392802 | 10/1990 | European Pat. Off. . |
| 0411615 | 2/1991 | European Pat. Off. . |
| 1532212 | 7/1968 | France . |
| 152027 | 6/1904 | Germany . |
| 208298 | 5/1984 | Germany . |
| 1178242 | 1/1970 | United Kingdom . |
| 9412165 | 6/1994 | WIPO . |
| 9421621 | 9/1994 | WIPO . |
| 9505363 | 2/1995 | WIPO . |
| 9509619 | 4/1995 | WIPO . |

OTHER PUBLICATIONS

Agarwal et al, Indian Journal of Chemistry, vol. 26 B, Jul. 1987, pp. 642–646.

Hoskinson et al, Journal of Textile Institute, vol. 64, 1973, pp. 144–152.

Mar., J., Advanced Organic Chemistry, 3d ed. John Willey and Sons, N.Y., 10, pp. 315, 1099, 1103–1104.

Bredt, et al., "Isolation if Nitric oxide sysnthetase, a calmodulin–requiring enzyme," Proc. Natl. Acad. Sci. (USA) 87: 682–685, 1990.

Förstermann, et al., "Calmodulin–dependent endothelium derived relaxing factor/nitric oximde synthetase activity . . . ," Proc. Natl. Acad. Sci. (USA) 88: 1788–1792, 1991.

Synthesis (1988), No. 6, pp. 460–466 (Rasmussen).

Hoskinson, "Studies on textile insectproofing . . ." Journal of the Textile Institute, vol. 64 No. 3, 1973, pp. 144–154.

Zhelyazov "Synthesis of substituted thiocarbamides and derivatives containing guaididne . . ." Chemical Abstracts, vol. 79 No. 5, Aug. 6, 1973.

Galstukhova "Synthesis of thiourea derivatives. VI 1-[2-(Methyl-thio)-5-pyrimidinyl] -3arylthiourea" Chemical Abstracts p. 318.

Mayrand "Urea and ehtylene glycol–facilitated transport systems in the human red cell membrane", Journal of General Physiology, vol. 81 No. 2, Feb. 1983 NY pp. 221–237.

*Primary Examiner*—Zinna Northington Davis
*Attorney, Agent, or Firm*—Nixon & Vanderhye

[57] ABSTRACT

There are provided novel compounds of formula I

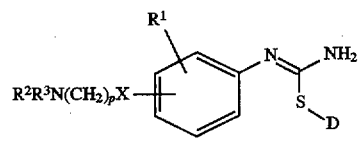

wherein D, $R^1$, $R^2$, $R^3$, X and p are as defined in the specification together with processes for their preparation, compositions containing them and their use in therapy.

Compounds of formula I are expected to be useful inter alia in the treatment of neurodegenerative disorders.

12 Claims, No Drawings

ISOTHIOUREA DERIVATIVES USEFUL IN THERAPY

This application is a 371 of PCT/SE95/01069, filed Sep. 20, 1995.

This invention relates to new isothiourea derivatives, processes for their preparation, compositions containing them and their use in therapy.

Thiourea and isothiourea derivatives have been described before for a variety of therapeutic uses. WO 94/12165 (Wellcome) describes simple isothiourea derivatives for use in the treatment of inter alia systemic hypotension, septic shock and inflammatory conditions; WO 95/09619 (Wellcome) (published after the priority date of this application) describes substituted urea and isothiourea derivatives for use in the treatment of cerebral ischaemia; United Kingdom Patent No 1178242 (Wellcome) discloses bisisothioureas having anti-inflammatory activity; European Patent Application No 411615 (Warner Lambert) discloses thiourea derivatives having use in the treatment of symptoms of cognitive decline; European Patent Application No 392802 (Beecham) discloses thiourea derivatives for use in the treatment of bronchial, cerebrovascular or neuronal disorders.

Isothiourea derivatives are also known as chemical intermediates in the preparation of guanidine derivatives (see U.S. Pat. No. 4,211,867 (McNeil Laboratories) and Synthesis (1988) 6, 460–466 (Rasmussen) which disclose the compound 4-dimethylaminophenylcarbamimidothioic acid methyl ester and U.S. Pat. No. 5,223,498 (Boots).

International Patent Applications WO 94/21621 and WO 95/05363 (Fisons Corporation) (both published after the priority date of this application) disclose guanidine and amidine compounds respectively which are indicated for the treatment of inter alia neurodegenerative disease.

We have now discovered a new and useful group of isothiourea derivatives.

According to a first aspect of the invention, we provide a compound of formula I

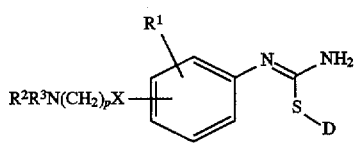

wherein
D represents alkyl C1 to 6;
$R^1$ represents hydrogen, alkyl C1 to 6 or halogen;
$R^2$ and $R^3$ independently represent hydrogen, alkyl C1 to 6, —(CH$_2$)$_r$A or
—(CH$_2$)$_m$OA;
or —NR$^2$R$^3$ together represent 1-indanyl or 1,2,3,4-tetrahydroisoquinolinyl; or
piperazinyl optionally 4-substituted by phenyl or alkyl C1 to 6;
A represents phenyl or a 5 membered heterocyclic aromatic ring containing 1 to 4 heteroatoms selected from O, S and N, which two groups are optionally substituted by one or more groups selected from alkyl C1 to 6, halogen and trifluoromethyl;
p, r and m independently represent an integer 0 to 4; and
X represents O or a bond; provided that
(a) when X represents O then p does not represent 0 or 1;
(b) when $R^1$ represents hydrogen, D represents methyl, X represents a bond attached to the phenyl ring in the para position and p represents 0, then $R^2$ and $R^3$ do not both represent methyl;

and pharmaceutically acceptable salts thereof.

We prefer that $R^2$ and $R^3$ independently represent hydrogen, alkyl C1 to 6 or —(CH$_2$)$_r$A or that —NR$^2$R$^3$ together represent 1,2,3,4-tetrahydroisoquinolinyl.

We prefer that A represents phenyl optionally substituted by one or more groups selected from alkyl C1 to 6, halogen and trifluoromethyl. We particularly prefer that A represents phenyl or phenyl substituted by chlorine.

We prefer that X represents a bond.

We prefer that $R^1$ represents hydrogen.

We prefer that X is orientated para to the N of the isothiourea moiety.

We prefer that p represents an integer 1 to 3, especially 2.

We prefer that D represents propyl or ethyl, particularly isopropyl or ethyl, especially ethyl.

According to the invention, we further provide a process for the preparation of compounds of formula I, and pharmaceutically acceptable salts thereof, which comprises:
(a) reacting a compound of formula II

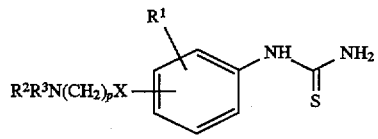

wherein $R^1$, $R^2$, $R^3$, p and X are as defined above with a compound of formula III

 D—L    III wherein D is as defined above and L is a leaving group,
(b) preparing a compound of formula I in which at least one of $R^2$ and $R^3$ represents alkyl C1 to 6, —(CH$_2$)$_r$A or —(CH$_2$)$_m$OA by reacting a corresponding compound of formula I in which one or both of $R^2$ and $R^3$ represents hydrogen with a compound of formula IV,

 $R^4$—L    IV wherein $R^4$ represents alkyl C1 to 6, —(CH$_2$)$_r$A or —(CH$_2$)$_m$OA and L is a leaving group,
(c) preparing a compound of formula I in which p represents an integer 1 to 4, by reduction of a compound of formula V

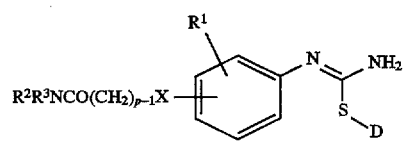

wherein D, X, $R^1$, $R^2$, $R^3$ and p are as defined above,
(d) preparation of a compound of formula I wherein both $R^2$ and $R^3$ represent hydrogen, by reduction of a corresponding compound of formula VI

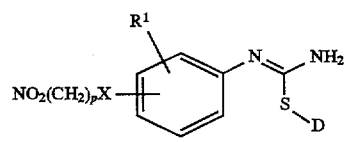

wherein $R^1$, D, p and X are as defined above,
(e) preparing a compound of formula I wherein $R^2$ represents hydrogen and p represents an integer 2 to 4, by reduction of a compound of formula VII

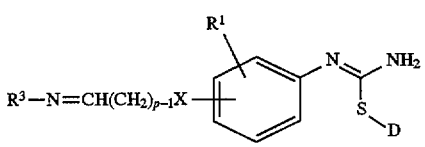

VII wherein $R^1$, $R^3$, D, X and p are as defined above, (f) preparing a compound of formula I wherein one of $R^2$ and $R^3$ represents hydrogen, and the other represents —$(CH_2)_rA$ in which r represents an integer 1 to 4, by reduction of a compound of formula VIII

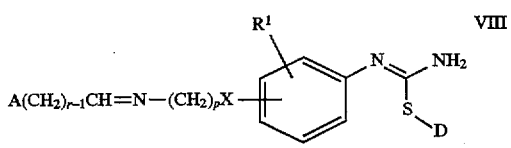

VIII wherein X, $R^1$, A, D, r and p are as defined above, (g) preparing a compound of formula I wherein one of $R^2$ and $R^3$ represents hydrogen, and the other represents —$(CH_2)_mOA$ in which m represents an integer 2 to 4, by reduction of a compound of formula IX

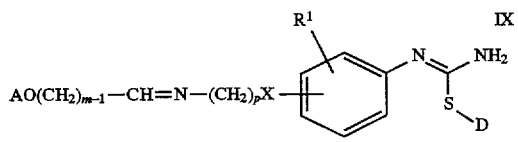

IX wherein X, $R^1$, A, D, p and m are as defined above, (h) preparing a compound of formula I wherein one of $R^2$ and $R^3$ represents hydrogen, and the other represents —$(CH_2)_rA$ in which r represents an integer 1 to 4, by reduction of a compound of formula X

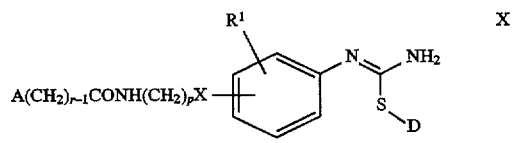

X wherein X, $R^1$, A, D, p and r are as defined above, or (i) preparing a compound of formula I wherein one of $R^2$ and $R^3$ represents hydrogen, and the other represents —$(CH_2)_rA$ in which m represents an integer 2 to 4, by reduction of a compound of formula X

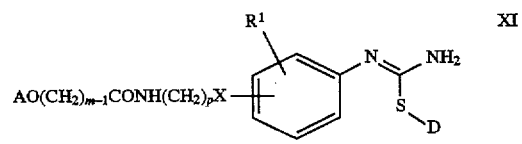

XI wherein X, $R^1$, A, D, p and m are as defined above, and where desired or necessary converting the resultant compound of formula I, or another salt thereof, to a pharmaceutically acceptable salt thereof, or vice versa.

In process (a) the reaction will proceed on combining the two reactants in an inert solvent e.g. acetone. Suitable leaving groups that L may represent include thioalkyl, sulphonic acid, trifluorocarbon sulphonic acid, halide, alkyl and aryl alcohols and tosyl groups; others are recited in 'Advanced Organic Chemistry', J. March (1985) 3rd Edition, McGraw-Hill on page 315 and are well known in the art. We prefer to use the iodide, toluenesulphonate or methane sulphonate derivative.

In process (b), the reaction will take place under standard conditions, for example by reacting the two materials in an inert solvent under basic conditions at room temperature for a period of up to 12 hours. We have frequently found it desirable to treat the amine with NaH before reacting with the compound of formula II. We prefer that L represents halide, particularly bromide.

In process (c), the reduction may be performed by treatment with diborane in an inert solvent e.g. THF. Alternative although less preferred reagents which may be suitable include lithium aluminium hydride and reagents for catalytic hydrogenation e.g. $H_2$ on Pd/C. Further details of the reaction conditions for use of these reactions may be obtained by reference to J. March "Advanced Organic Chemistry" on page 1099, including the references cited therein.

In process (d), the reduction reaction may be performed under a number of conditions, for example those described in J March "Advanced Organic Chemistry" on pages 1103–1104. These include catalytic hydrogenation, use of Zn, Sn or Fe metal, $AlH_3$—$AlCl_3$, sulphides and others. We prefer to perform the reaction by hydrogenation at atmospheric pressure for 3–6 hours in the presence of a palladium and carbon catalyst.

In processes (e), (f) and (g), the reduction may be performed by treating the compound with sodium borohydride under standard conditions.

In processes (h) and (i), the reaction may be performed under conditions analogous to those described above for process (c).

Compounds of formula II are new except for one compound disclosed in Synthesis (1988) 6, 460–466 (Rasmussen). Therefore as a further aspect of the invention we provide a compound of formula II, or a salt thereof, provided that when $R^1$ represents hydrogen, X represents a bond attached to the phenyl ring in the para position and p represents 0, then $R^2$ and $R^3$ do not both represent methyl.

Compounds of formula II may be prepared following the method of Rasmussen et al in Synthesis (1988) 456–459. Compounds of formula II can thus be prepared by reacting a compound of formula XII

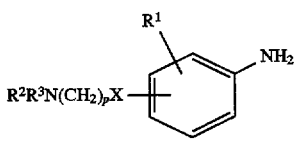

XII wherein $R^1$, $R^2$, $R^3$, p and X are as defined above, with benzoyl isothiocyanate in an organic solvent such as acetone optionally in the presence of acid (e.g. trifluoroacetic acid) followed by aqueous-alkaline cleavage of the resultant benzoylthiourea derivative. Compounds of formula II may also be prepared by reacting a compound of formula XII with sodium thiocyanate in water.

Compounds of formula III, IV, VI and XII are either known or may be prepared by conventional methods known per se. For example, compounds of formula XII may be prepared by reduction of the corresponding nitrophenyl derivative. These nitrophenyl derivatives are either known or may be prepared from another nitrophenyl derivative with a simpler sidechain following a process analogous to one of processes (c) to (i) above. For example, compounds of formula XII in which X represents O may be prepared by reacting a hydroxynitrophenol with a compound of formula XIII $R^2R^3N(CH_2)_pL$      XIII wherein $R^2$, $R^3$ and p are as defined above and L is a leaving group of the type mentioned above.

Conditions suitable for this reaction will be well known to a person skilled in the art.

Compounds of formula VII, VIII, IX, X, XI and XIII are also either known or may be prepared by conventional methods known per se. For example, amides of formula X and XI may be made by reaction of a corresponding acid or activated acid with an corresponding amine. Imines of formula VII, VIII and IX may be made by reaction of a corresponding aldehyde with the corresponding amine.

Salts of compounds of formula I may be formed by reacting the free acid, base or a salt, enantiomer, tautomer or protected derivative thereof, with one or more equivalents of the appropriate base or acid. The reaction may be carried out in a solvent or medium in which the salt is insoluble or in a solvent in which the salt is soluble, eg water, dioxan, ethanol, tetrahydrofuran or diethyl ether, or a mixture of solvents, which may be removed in vacuo or by freeze drying. The reaction may be a metathetical process or it may be carried out on an ion exchange resin.

It will be apparent to a person skilled in the art that it may be desirable to protect an amine or other reactive group in an intermediate compound using a protecting group as described in the standard text "Protecting groups in Organic Synthesis", 2nd Edition (1991) by Greene and Wuts. Amine-protecting groups which may be mentioned include alkyloxycarbonyl C2 to 7, eg t-butyloxycarbonyl, phenylalkyloxycarbonyl C8 to 13, eg benzyloxycarbonyl or preferably trifluoroacetate. Deprotection will normally take place on treatment with aqueous base.

The compounds of the invention and intermediates may be isolated from their reaction mixtures by standard techniques.

The term "alkyl C1 to 6" includes straight chain, branched, saturated, unsaturated, aliphatic and cyclic alkyl groups containing 1 to 6 carbon atoms.

The compounds of formula I may exist in tautomeric, enantiomeric or diasteriomeric forms, all of which are included within the scope of the invention. The various optical isomers may be isolated by separation of a racemic mixture of the compounds using conventional techniques, e.g. fractional crystallisation, or HPLC. Alternatively the individual enantiomers may be made by reaction of the appropriate optically active starting materials under reaction conditions which will not cause racemisation.

Intermediate compounds may also exist in enantiomeric forms and may be used as purified enantiomers, diastereomers, racemates or mixtures.

The compounds of general formula I possess useful pharmacological activity in animals. In particular, they possess useful nitric oxide synthase inhibiting activity, and are expected to be useful in the treatment or prophylaxis of human diseases or conditions in which the synthesis or over synthesis of nitric oxide forms a contributory part; for example, hypoxia, e.g. in cases of cardiac arrest, stroke and neonatal hypoxia, neurodegenerative conditions including nerve degeneration and/or nerve necrosis in disorders such as ischaemia, hypoxia, hypoglycemia, epilepsy, and in external wounds (such as spinal cord and head injury), hyperbaric oxygen convulsions and toxicity, dementia e.g. pre-senile dementia, Alzheimer's disease and AIDS-related dementia, Sydenham's chorea, Parkinson's disease, Huntington's disease, Amyotrophic Lateral Sclerosis, Korsakoff's disease, imbecility relating to a cerebral vessel disorder, sleeping disorders, schizophrenia, anxiety, depression, seasonal affective disorder, jet-lag, depression or other symptoms associated with Premenstrual Syndrome (PMS), anxiety and septic shock. Compounds of formula I may also be expected to show activity in the prevention and reversal of tolerance to opiates and diazepines, treatment of drug addiction, relief of pain and treatment of migraine and other vascular headaches. The compounds of the present invention may also show useful immunosuppressive activity, be useful in the treatment or prophylaxis of inflammation, in the treatment of of gastrointestinal motility disorders, and in the induction of labour. The compounds may also be useful in the treatment of cancers that express nitric oxide synthase.

Compounds of formula I are expected to be particularly useful in the treatment or prophylaxis of neurodegenerative conditions or of migraine or for the prevention and reversal of tolerance to opiates and diazepines or for the treatment of drug addiction and especially in the treatment or prophylaxis of neurodegenerative disorders. We are particularly interested in conditions selected from the group consisting of hypoxia, ischaemia, stroke and Amyotrophic Lateral Sclerosis.

Thus according to a further aspect of the invention we provide a compound of formula I without proviso (b), or a pharmaceutically acceptable salt thereof, for use as a pharmaceutical.

According to another feature of the invention we provide the use of a compound of formula I without proviso (b), or a pharmaceutically acceptable salt thereof, in the manufacture of a medicament for the treatment or prophylaxis of the aforementioned diseases or conditions; and a method of treatment or prophylaxis of one of the aforementioned diseases or conditions which comprises administering a therapeutically effective amount or a compound of formula I without proviso (b), or a pharmaceutically acceptable salt thereof, to a person suffering from or susceptible to such a disease or condition.

For the above mentioned therapeutic indications, the dosage administered will, of course, vary with the compound employed, the mode of administration and the treatment desired. However, in general, satisfactory results are obtained when the compounds are administered to a human at a daily dosage of between 1 mg and 2000 mg (measured as the solid form) per day.

The compounds of formula I, and pharmaceutically acceptable salts thereof, may be used on their own, or in the form of appropriate medicinal preparations for enteral or parenteral administration.

According to the invention, there is provided a pharmaceutical formulation including preferably less than 80% and more preferably less than 50% of a compound of formula I without proviso(b), or a pharmaceutically acceptable salt thereof, in admixture with a pharmaceutically acceptable diluent or carrier.

We also provide a method of preparation of such a pharmaceutical formulation which comprises mixing the ingredients.

Examples of such diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include: tablets, capsules and dragees; sustained release compositions include those in which the active ingredient is bound to an ion exchange resin which is optionally coated with a diffusion barrier to modify the release properties of the resin.

The enzyme nitric oxide synthase has a number of isoforms and compounds of formula I, and pharmaceutically acceptable salts thereof, may be screened for nitric oxide synthase inhibiting activity by procedures based on those of Bredt and Snyder in Proc. Natl. Acad. Sci. (1990) 87, 682–685 and Förstermann et. al., Eur. J. Pharm. (1992) 225, 161–165 as follows. Nitric oxide synthase converts $^3$H-L-arginine to $^3$H-L-citrulline which can be separated by cation exchange chromatography and quantified by scintillation counting.

Screen A (A) Screen for neuronal nitric oxide synthase inhibiting activity

Enzyme was isolated from rat hippocampus or cerebellum. The cerebellum or hippocampus of a male Sprague-Dawley rat (250–275 g) is removed following $CO_2$ anaesthesia of the animal and decapitation. Cerebellar or hippocampal supernatant is prepared by homogenisation in 50 mM Tris-HCl with 1 mM EDTA buffer (pH 7.2 at 25° C.) and centifugation for 15 minutes at 20,000 g. Residual L-arginine is removed from the supernatant by chromatography through Dowex AG-50W-X8 sodium form and hydrogen form columns successively, and further centrifugation at 1000 g for 30 seconds.

For the assay, 25 µl of the final supernatant is added to each of 12 test tubes containing 25 µl L-arginine solution (of concentration 18 µM $^1$H-L-arginine, 96 nM $^3$H-L-arginine) and either 25 µl of an assay buffer (50 mM HEPES, 1 mM EDTA, 1.5 mM $CaCl_2$, pH 7.4) or 25 µl of test compound in the buffer at 22° C. To each test tube is added 75 µl of complete assay buffer (50 mM HEPES, 1 mM EDTA, 1.5 mM $CaCl_2$, 1 mM DTT, 100 µM NADPH, 10 µg/ml calmodulin, pH 7.4) to initiate the reaction and the reaction is stopped after 10 minutes by addition of 2 ml of a termination buffer (20 mM HEPES, 2 mM EDTA, pH 5.5).

Labelled L-citrulline is separated from labelled L-arginine by chromatography over a Dowex AG-50W-X8 200-400 mesh column. 1 ml of each terminated reaction is added to an individual 1 ml column and the eluant combined with that from two 1 ml distilled water washes and 16 ml of scintillation cocktail. The L-citrulline is then quantified by scintillation counting.

In a typical experiment using the cerebellar supernatant, basal activity is increased by 20,000 dpm/ml of sample above a reagent blank which has an activity of 7,000 dpm/ml. A reference standard, N-nitro-L-arginine, which gives 60% inhibition of nitric oxide synthase at a concentration of 1 µM, is tested in the assay to verify the procedure.

Screen B (B) Screen for macrophage nitric oxide synthase inhibiting activity

Enzyme is prepared, after induction, from the cultured murine macrophage cell line J774A-1 (obtained from laboratories of the Imperial Cancer Research Fund). J774A-1 cells are cultured in Dulbecco's Modified Eagles Medium (DMEM) supplemented with 10% foetal bovine serum, 4 mM L-glutamine and antibiotics (100 units/ml penicillin G, 100 µg/ml streptomycin & 0.25 µg/ml amphotericin B). Cells are routinely grown in 225 $cm^3$ flasks containing 35 ml medium kept at 37° C. and in a humidified atmosphere containing 5% $CO_2$.

Nitric oxide synthase is produced by cells in response to interferon-γ (IFNγ) and lipopolysaccharide (LPS). The medium from confluent culture flasks is removed and replaced with 25 ml (per flask) of fresh medium containing 1 µg/ml LPS and 10 units/ml IFNγ. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 µM dithiothreitol and a cocktail of protease inhibitors comprising leupeptin (2 µg/ml), soya bean trypsin inhibitor (10 µg/ml), aprotinin (5 µg/ml) & phenylmethylsulphonyl fluoride (50 µg/ml).

For the assay, 25 µl substrate cocktail (50 mM Tris-HCl (pH 7.5 at 20° C.), 400 µM NADPH, 20 µM flavin adenine dinucleotide, 20 µM flavin mononucleotide, 4 µM tetrahydrobiopterin, 12 µM L-arginine and 0.025 µCi L-[$^3$H] arginine) is added to wells of a 96 well filter plate (0.45 µM pore size) containing 25 µl of a solution of test compound in 50 mM Tris-HCl. The reaction is started by adding 50 µl of cell lysate (prepared as above) and after incubation for 1 hour at room temperature is terminated by addition of 50 µl of an aqueous solution of 3 mM nitroarginine and 21 mM EDTA.

Labelled L-citrulline is separated from labelled L-arginine using Dowex AG-50W. 150 µl of a 25% aqueous slurry of Dowex 50W ($Na^+$ form) is added to the assay after which the whole is filtered into 96 well plates. 70 µl of filtrate is sampled and added to wells of 96 well plates containing solid scintillant. After allowing the samples to dry the L-citrulline is quantified by scintillation counting.

In a typical experiment basal activity is 300 dpm per 70 µl sample which is increased to 1900 dpm in the reagent controls. Aminoguanidine, which gives an $IC_{50}$ (50% inhibitory concentration) of 10 µM, is tested as a standard to verify the procedure.

Screen C (C) Screen for endothelial nitric oxide synthase inhibiting activity

Enzyme may be isolated from human umbilical vein endothelial cells (HUVECs) by a procedure based on that of Pollock et al (1991) Proc. Nat. Acad. Sci., 88, 10480–10484. HUVECs were purchased from Clonetics Corp (San Diego, Calif., USA) and cultured to confluency. Cells can be maintained to passage 35–40 without significant loss of yield of nitric oxide synthase. When cells reach confluency, they are resuspended in Dulbecco's phosphate buffered saline, centrifuged at 800 rpm for 10 mins, the cell pellet homogenised in ice-cold 50 mM Tris-HCl, 1 mM EDTA, 10% glycerol, 1 mM phenylmethylsulphonylfluoride, 2 µM leupeptin at pH 4.2. Following centrifugation at 34,000 rpm for 60 mins, the pellet is solubilised in the homogenisation buffer which also contains 20 mM CHAPS. After a 30 min incubation on ice, the suspension is centrifuged at 34,000 rpm for 30 mins. The resulting supernatant is stored at −80° C. until use.

For the assay, 25 µl of the final supernatant is added to each of 12 test tubes containing 25 µl L-arginine solution (of concentration 12 µM $^1$H-L-arginine, 64 nM $^3$H-L-arginine) and either 25 µl of an assay buffer (50 mM HEPES, 1 mM EDTA, 1.5 mM $CaCl_2$, pH 7.4) or 25 µl of test compound in the buffer at 22° C. To each test tube was added 25 µl of complete assay buffer (50 mM HEPES, 1 mM EDTA, 1.5 mM $CaCl_2$, 1 mM DTF, 100 µM NADPH, 10 µg/ml calmodulin, 12 µM tetrahydrobiopterin, pH 7.4) to initiate the reaction and the reaction is stopped after 10 mins by addition of 2 ml of a termination buffer (20 mM HEPES, 2 mM EDTA, pH 5.5).

Labelled L-citrulline is separated from labelled L-arginine by chromatography over a Dowex AG-50W-X8 200-400 mesh column. 1 ml of each terminated reaction is added to an individual 1 ml column and the eluant combined with that from two 1 ml distilled water washes and 16 ml of scintillation cocktail. The L-citrulline is then quantified by scintillation counting.

In a typical experiment, basal activity is increased by 5,000 dpm/ml of sample above a reagent blank which has an activity of 1500 dpm/ml. A reference standard, N-nitro-L-arginine, which gives 70–90% inhibition of nitric oxide synthase at a concentration of 1 µM, is tested in the assay to verify the procedure.

Compounds may also be tested in an ex-vivo assay to determine the extent of brain penetration.

Screen D (D) Ex vivo assay for neuronal nitric oxide synthase inhibiting activity Male Sprague-Dawley rats (250–275 g) were dosed intravenously at 10 mg/kg with test compound dissolved in 0.9% saline or with saline alone as control. At a predetermined time (typically 2–24 hours) after treatment, the animals were sacrificed, the cerebellum removed and the supernatant prepared and assayed for nitric oxide synthase activity as described in Screen A.

As a further confirmatory test, a fraction of the cerebellar supernatant was applied to a 2'–5'-ADP Sepharose column (which binds nitric oxide synthase) and subsequently eluted with NADPH. The eluant was tested for nitric oxide synthase activity following the procedure of Screen A.

Compounds that penetrate the rat brain and inhibit neuronal nitric oxide synthase resulted in reduced nitric oxide synthase activity both in the supernatant preparation and in the eluant from the 2'–5'-ADP Sepharose column.

In the screens for nitric oxide synthase inhibition activity, compound activity is expressed as $IC_{50}$ (the concentration of drug substance which gives 50% enzyme inhibition in the assay). $IC_{50}$ values for test compounds were initially estimated from the inhibiting activity of 1, 10 and 100 µM solutions of the compounds. Compounds that inhibited the enzyme by at least 50% at 10 µM were retested using more appropriate concentrations so that an $IC_{50}$ could be determined.

In Screen A above (a screen for activity against the neuronal isoform of nitric oxide synthase), the compound of Example 1 below gave an $IC_{50}$ of less than 10 µM indicating that it is expected to show useful therapeutic activity. In Screens B and C (the screens for activity against the macrophage and endothelial isoforms of nitric oxide synthase) the compound of Example 1 gave $IC_{50}$ values more than 10 times that obtained in Screen A indicating that it shows desirable selectivity.

The compounds of Examples 2–4 were also tested in Screen A and also gave $IC_{50}$ values of less than 10 µM. Thus these compounds are also expected to show useful therapeutic activity.

When compared with compounds of the prior art, the compounds of formula I, and pharmaceutically acceptable salts thereof, have the advantage that they may be less toxic, be more efficacious, be longer acting, have a broader range of activity, be more potent, be more selective for the neuronal isoform of nitric oxide synthase enzyme, produce fewer side effects, be more easily absorbed or have other useful pharmacological properties.

The invention is illustrated by the following examples:

EXAMPLE 1

N-(4-(2-((Phenylmethyl)(methyl)amino)ethyl) phenyl)carbamimidothioic acid ethyl ester (a) 4-Nitrophenylacetyl chloride A stirred mixture of 4-nitrophenylacetic acid (25 g, 0.138 mol) in thionyl chloride (50 ml, 0.685 mol) was heated at reflux for 2 hours then concentrated to yield 4-nitrophenylacetyl chloride (27.55 g) as a tan solid.

(b) N-Benzyl-N-methyl-4-nitrophenylacetamide

To a stirred solution of N-benzylmethylamine (47.6 ml, 0.369 mol) in methylene chloride (400 ml) was added 4-nitrophenylacetyl chloride (step (a), 24.86 g, 0.125 mol), dissolved in methylene chloride (100 ml), at a rate as to maintain the temperature at 20°–28° C. with ice bath cooling. After stirring for 2 hours, the reaction mixture was washed successively with 1.25N hydrochloric acid, water, 1N sodium hydroxide and finally with water. The methylene chloride solution was dried over anhydrous magnesium sulfate and concentrated to an oil on a rotary evaporator. The oil was dissolved in ether (100 ml) from which N-benzyl-N-methyl-4-nitrophenylacetamide crystallized rapidly, yield 31.5 g (89%).

(c) N-Benzyl-N-methyl[2-(4-nitrophenyl)ethyl]amine

To a stirred solution of N-benzyl-N-methyl-4-nitrophenylacetamide (step (b), 24.9 g, 87.6 mmol) in tetrahydrofuran (270 ml) under nitrogen, was added dropwise 1.0M borane-tetrahydrofuran (245 ml, 245 mmol). The reaction was heated at reflux for 2 hours, cooled, then methanol (53 ml) was added dropwise followed by the cautious addition of aqueous 2.5N hydrochloric acid (100 ml). The resulting mixture was refluxed for 1 hour and then concentrated on a rotary evaporator to remove the organic solvents. Water was added to the residue and the mixture was basified to pH 11 with 2.5N aqueous sodium hydroxide. The product was then extracted into three portions of methylene chloride. The combined extracts were washed with water, dried over magnesium sulfate, filtered and concentrated to yield 23.7 g (100%) of N-benzyl-N-methyl [2-(4-nitrophenyl)ethyl]amine. The hydrochloride salt, prepared in methanol and recrystallized from 95% ethanol-ether, melted at 222°–4° C. (dec).

(d) 4-(2-((phenylmethyl)(methyl)amino)ethyl) phenylamine

To a solution of N-benzyl-N-methyl[2-(4-nitrophenyl) ethyl]amine (3.9 g, 14.4 mmol) in 85% acetic acid (250 ml) was added in one portion zinc dust (9.4 g, 144 mmol). The reaction was stirred for 30 minutes, filtered, and concentrated. The residue was dissolved in water (50 ml), the solution basified with 2.5N aqueous sodium hydroxide and the mixture extracted with several portions of methylene chloride. The combined organic layers were dried over magnesium sulfate, filtered and concentrated to yield 4-(2-((phenylmethyl)(methyl)amino)ethyl)phenylamine (3.41 g, 98%). The dihydrochloride salt, from methanol-ethyl acetate, melted at 275° C. (dec).

(e) 3-(4-(2-((phenylmethyl)(methyl)amino)ethyl)phenyl)-1-benzoyl-2-thiourea

To a solution of benzoyl isothiocyanate (1.67 ml, 12.4 mmol) in dry acetone (10 ml), preheated to a very gentle reflux, was added rapidly, at a rate as to control a vigorous reflux, the product of step (d), 2.23 g, 9.28 mmol) dissolved in dry acetone (5.0 ml). The reaction mixture was refluxed for 30 minutes and then poured onto ice with vigorous stirring. The resulting solid was collected, washed with water and recrystallized from isopropanol (35 ml) to yield 3-(4-(2-((phenylmethyl)(methyl)amino)ethyl)phenyl)-1-benzoyl-2-thiourea (2.2 g).

(f) 1-(4-(2-((Phenylmethyl)(methyl)amino)ethyl)phenyl)-2-thiourea

A mixture of 3-(4-(2-(benzylmethylamino)ethyl)phenyl)-1-benzoyl-2-thiourea (step (e), 2.4 g, 5.95 mmol) and 2.5N aqueous sodium hydroxide (20 ml) was heated at 90° C. for 35 minutes with stirring. The warm reaction mixture was then poured into water (60 ml) with stirring. The product was extracted into three portions of methylene chloride. The combined extracts were washed with water, dried over magnesium sulfate and concentrated to dryness to yield 1.71 g of crude 1-(4-(2-((phenylmethyl)(methyl)amino)ethyl)phenyl)-2-thiourea. The product was crystallized from benzene, m.p. 119°–21.5° C.

(g) N-(4-(2-((Phenylmethyl)(methyl)amino)ethyl)phenyl) carbamimidothioic acid ethyl ester 1-(4-(2-((Phenylmethyl)(methyl)amino)ethyl)phenyl)-2-thiourea (step (f), 0.30 g) was suspended in 200 ethanol (2.5 ml), and the mixture was treated with methanesulfonic acid (0.065 ml) and then ethyl methanesulfonate (0.12 ml). After 3 hours at 100° C., TLC on C18 silica with 80% methanol/ 20% water with 0.8% ammonium acetate showed incomplete conversion to product. At this point additional ethyl methanesulfonate (0.20 g) was added and the mixture refluxed for one hour. After stirring overnight, the crude reaction product was treated with ethyl acetate (50 ml) and water (50 ml). The aqueous layer was treated with sodium carbonate (0.25 g) and extracted with diethyl ether (20 ml). The remaining aqueous layer was treated with sodium bicarbonate (1 g) and extracted with of diethyl ether (20 ml). The ether layers were identical by TLC and were combined, dried with sodium sulfate and evaporated to yield the free base which was then treated with maleic acid (0.24 g) in methanol (1 ml), then diluted with ethyl acetate (4 ml) followed by diethyl ether (25 ml), giving an oil. The solvents were decanted, and the resulting solids were dissolved in hot isopropanol (20 ml) and cooled to −20° C. The resulting solids were collected and air dried to provide N-(4-(2-((phenylmethyl)(methyl)amino)ethyl)phenyl) carbamimidothioic acid, ethyl ester, 0.34 g, m.p. 136°–137° C.

EXAMPLE 2

N-(4-(2-((Phenylmethyl)(methyl)amino)ethyl) phenyl)carbamimidothioic acid isopropyl ester dimaleate To a stirred mixture of the compound of Example 1(f) (250 mg, 0.835 mmol) and isopropanol (6.0 ml) was added methanesulfonic acid (54.2 µl, 0.835 mmol). After stirring for a few minutes, 2-iodopropane (250 µl, 2.51 mmol) was added. The reaction mixture was refluxed, with stirring, for 24 hours. Ether (100 ml) was added to the cooled reaction mixture to precipitate the salts of the product. The clear supernatant liquid was decanted from the oily residue. The residue was then dissolved in water (15 ml) and the solution clarified through celite. The clear aqueous solution was basideal with a saturated solution of sodium bicarbonate. The free base of the product was extracted into methylene chloride, the solution dried over anhydrous magnesium sulfate and the solvent was removed under vacuum to yield 0.2688 g (94.3%) of product as an oil. This was dissolved in ethanol (3.0 ml), maleic acid (0.201 g) was added and the mixture was warmed to obtain complete solution. Ether (4.0 ml) was added and crystallization initiated; to yield 338 mg of N-(4-(2-((phenylmethyl)(methyl)amino)ethyl)phenyl) carbamimidothioic acid isopropyl ester dimaleate, m.p. 125°–7° C.

EXAMPLE 3

N-(4-(2-(3-Chlorobenzylamino)ethyl)phenyl) carbamimidothioic acid ethyl ester dimethanesulfonate (a) 3-Chlorobenzyl[2-(4-nitrophenyl)ethyl]amine This was prepared following a method analogous to that of Example 1, steps (a)–(c).

(b) N-(3-Chlorobenzyl)-N-2-4-nitrophenyl)ethyl trifluoroacetamide

To a stirred solution of the product of step (a) (5.82 g, 20.0 mmol) and triethylamine (3.21 ml, 23.0 mmol) in methylene chloride (15 ml) was added trifluoroacetic anhydride (4.63 g, 22.0 mmol) dropwise, with cooling and stirring. After stirring for 1.5 hours at room temperature, the reaction mixture was washed with water, dried over anhydrous magnesium sulfate, filtered and concentrated to yield 7.7 g of N-(3-chlorobenzyl)-N-(2-(4-nitrophenyl)ethyl)trifluoroacetamide as a thick oil.

(c) N-(3-Chlorobenzyl)-N(2-(4-aminophenyl)ethyl) trifluoroacetamide

To a solution of the product of step (b) (3.89 g, 10.05 mmol) in ethyl acetate (100 ml) was added 5% Pd/C. The mixture was hydrogenated at 50 psig for 1.4 hours, until the theoretical amount of hydrogen was taken up. The catalyst was filtered and the filtrate concentrated to an oil. This was purified by chromatography (silica gel, methylene chloride: n-hexane (1:1)) to yield 2.33 g of pure N-(3-chlorobenzyl)-N-(2-(4-aminophenyl)ethyl)trifluoroacetamide as a thick oil.

(d) N-(2-(4-(3-Benzoylthioureido)phenyl)ethyl)-N-(3-chlorobenzyl)-trifluoroacetamide This was prepared from the product of step (c) following a method analogous to that of Example 1, step (e). The product was isolated as a thick oil.

(e) 1-(4-(2-3-Chlorobenzylamino)ethyl)phenyl-2-thiourea

This was prepared from the product of step (d) following a method analogous to that of Example 1 step (f). The product was purified by chromatography (silica gel, 2% methanol saturated with ammonia in ether) to yield 0.5 g of pure 1-(4-(2-(3-chlorobenzylamino)ethyl)phenyl)-2-thiourea. This was recrystallized from benzene, m.p. 132°–4° C.

(f) N-(4-(2-(3-Chlorobenzylamino)ethyl)phenyl) carbamimidothioic acid ethyl ester dimethanesulfonate To a stirred mixture of the product of step (e) (272.5 mg, 0.852 mmol) and ethanol (2.6 ml) was added methanesulfonic acid (81.88 mg, 0.852 mmol). After stirring for a few minutes, ethyl methanesulfonate (211.6 mg, 1.70 mmol) was added. The reaction mixture was refluxed, with stirring, for 3 hours. Additional ethyl methanesulfonate (117 mg) was added and refluxing continued for 2 hours to complete the reaction. On cooling, the product crystallized to a thick mass. Ether was added and the product was isolated by filtration and then recrystallized from ethanol-ether to yield 407.3 mg of N-(4-(2-(3-chlorobenzylamino)ethyl)phenyl) carbamimidothioic acid ethyl ester dimethanesulfonate, m.p. 173°–5° C.

EXAMPLE 4

N-(4-(2-(1,2,3,4-Tetrahydroisoquinolin-2-yl)ethyl) phenyl)carbamimidothioic acid ethyl ester dimaleate (a) 2-(4-Nitrophenethl)-1,2,3,4-tetrahydroisoquinoline This was prepared from 1,2,3,4-tetrahydroisoquinoline following a method analogous to that of Example 1 steps, (a)–(c).

(b) 2-(4-Aminophenethyl)-1,2,3,4-tetrahydroisoquinoline dihydrochloride

To a solution of the product of step (a) (11.0 g, 39.0 mmol) in 95% ethanol (150 ml), concentrated hydrochloric acid (7.5 ml) and water (50 ml) was added 10% Pd/C (1.0 g). The mixture was hydrogenated at 50 psig for 2.5 hours, until the theoretical amount of hydrogen was taken up. The catalyst was filtered and the filtrate concentrated to a solid residue. This was digested in absolute ethanol (75 ml), cooled, filtered and air dried; yield 11.4 g (90%) of the dihydrochloride salt.

(c) 1-(4-(2-1,2,3,4-Tetrahydroisoquinolin-2-yl)ethyl)phenyl)-2-thiourea

This was prepared from the product of step (b) (as the free base) following a method analogous to that of Example 1, steps (e)–(f). The product was crystallized from methylene chloride, m.p. 165°–9° C.

(d) N-(4-(2-(1,2,3,4-Tetrahydroisoquinolin-2-yl)ethyl)phenyl)carbamimidothioic acid ethyl ester dimaleate This was prepared from the product of step (c) following a method analogous to that of Example 3, step (f). The reaction was worked up to yield an oil of the free base. This was purified by chromatography (silica gel, 20% ether saturated with ammonia in methylene chloride). The dimaleate salt was prepared in ethanol and precipitated out with ether; m.p. 123°–5° C.

I claim:

1. A compound of formula I:

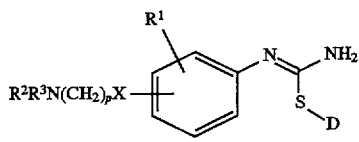

wherein

D represents alkyl C1 to 6;

$R^1$ represents hydrogen, alkyl C1 to 6 or halogen;

$R^2$ and $R^3$ independently represent hydrogen, alkyl C1 to 6, —$(CH_2)_rA$ or —$(CH_2)_mOA$;

or —$NR^2R^3$ together represent 1,2,3,4-tetrahydroisoquinolinyl or piperazinyl optionally 4-substituted by phenyl or alkyl C1 to 6;

A represents phenyl or a 5 membered heterocyclic aromatic ring containing 1 to 4 heteroatoms selected from O, S and N, which two groups are optionally substituted by one or more groups selected from alkyl C1 to 6, halogen and trifluoromethyl; p, r and m independently represent an integer 0 to 4; and X represents O or a bond;

provided that (a) when X represents O then p does not represent 0 or 1;

(b) when $R^1$ represents hydrogen, D represents methyl, X represents a bond attached to the phenyl ring in the para position and p represents 0, then $R^2$ and $R^3$ do not both represent methyl;

or a pharmaceutically acceptable salt thereof.

2. A compound of formula I, according to claim 1 wherein X represents a bond.

3. A compound of formula I, according to claim 1 or claim 2, wherein D represents ethyl or propyl.

4. A compound of formula I, according to claim 3, wherein D represents ethyl.

5. A compound of formula I, according to claim 1, wherein p represents an integer 1 to 3.

6. A compound of formula I, according to claim 1, wherein $R^2$ and $R^3$ independently represent hydrogen, alkyl C1 to 6 or —$(CH_2)_rA$ or —$NR^2R^3$ together represents 1,2,3,4-tetrahydroisoquinolinyl.

7. A compound of formula I according to claim 1, which is:

N-(4-(2-((Phenylmethyl)(methyl)amino)ethyl)phenyl)carbamimidothioic acid ethyl ester;

N-(4-(2-((Phenylmethyl)(methyl)amino)ethyl)phenyl)carbamimidothioic acid isopropyl ester;

N-(4-(2-(3-Chlorobenzylamino)ethyl)phenyl)carbamimidothioic acid ethyl ester;

N-(4-(2-(1,2,3,4-Tetrahydroisoquinolin-2-yl)ethyl)phenyl)carbamimidothioic acid ethyl ester;

or a pharmaceutically acceptable salt of any one thereof.

8. A pharmaceutical composition including the compound formula I

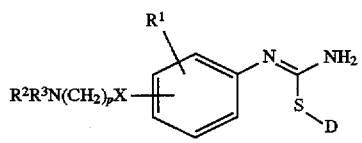

wherein D represents alkyl C1 to 6;

$R^1$ represents hydrogen, alkyl C1 to 6 or halogen;

$R^2$ and $R^3$ independently represent hydrogen, alkyl C1 to 6, —$(CH_2)_rA$ or —$(CH_2)_mOA$;

or —$NR^2R^3$ together represent 1,2,3,4-tetrahydroisoquinolinyl or piperazinyl optionally 4-substituted by phenyl or alkyl C1 to 6;

A represents phenyl or a 5 membered heterocyclic aromatic ring containing 1 to 4 heteroatoms selected from O, S and N, which two groups are optionally substituted by one or more groups selected from alkyl C1 to 6, halogen and trifluoromethyl;

p, r and m independently represent an integer 0 to 4; and X represents O or a bond;

provided that when X represents O then p does not represent 0 or 1;

or a pharmaceutically acceptable salt thereof, in admixture with a pharmaceutically acceptable diluent or carrier.

9. A method of treatment of neurodegenerative disorders, migraine, drug addition, or the reversal of tolerance to opiates and diazepines which comprises administering to a patient a therapeutically effective amount of a compound of formula I

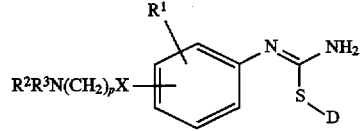

wherein D represents alkyl C1 to 6;

$R^1$ represents hydrogen, alkyl C1 to 6 or halogen;

$R^2$ and $R^3$ independently represent hydrogen, alkyl C1 to 6, —$(CH_2)_rA$ or —$(CH_2)_mOA$;

or —$NR^2R^3$ together represent 1,2,3,4-tetrahydroisoquinolinyl or piperazinyl optionally 4-substituted by phenyl or alkyl C1 to 6;

A represents phenyl or a 5 membered heterocyclic aromatic ring containing 1 to 4 heteroatoms selected from O, S and N, which two groups are optionally substituted by one or more groups selected from alkyl C1 to 6, halogen and trifluoromethyl; p, r and m independently represent an integer 0 to 4; and X represents O or a bond;

provided that when X represents O then p does not represent 0 or 1;

or a pharmaceutically acceptable salt thereof.

10. A process for the preparation of a compound of formula I, as defined in claim 1, and pharmaceutically acceptable salt thereof, which comprises:

reacting a compound of formula II

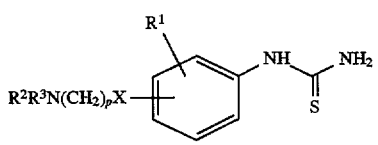

wherein $R^1$, $R^2$, $R^3$, p and X are as defined in claim 1, with a compound of formula III

D—L                                         III wherein D is as defined in claim 1 and L is a leaving group.

11. A process according to claim 10, wherein an acid is present.

12. A process according to claim 11, wherein said acid is methanesulfonic acid.

* * * * *